(12) United States Patent
Eisenbrand et al.

(10) Patent No.: US 6,664,285 B1
(45) Date of Patent: Dec. 16, 2003

(54) USE OF CELL MEMBRANE PENETRATING INDIGOID BISINDOLE DERIVATIVES

(76) Inventors: Gerhard Eisenbrand, Gustav Kirchhoffstrasse 3, D-69120 Heidelberg (DE); Heinz Herbert Fiebig, Institut für Experimentelle Onkologie, Am Flughafen 8-10, D-79110 Freiburg (DE); Doris Marko, An der Emilsruhe 36, D-67657 Kaiserslautern (DE); Ralf Hössel, Am Rödelheimer Wehr 3, D-60489 Frankfurt am Main (DE); Weici Tang, Theodor-Heuss-Strasse 11, D-67663 Kaiserslautern (DE)

( * ) Notice: Subject to any disclaimer, the term of this patent is extended or adjusted under 35 U.S.C. 154(b) by 0 days.

(21) Appl. No.: 09/958,674

(22) PCT Filed: Apr. 11, 2000

(86) PCT No.: PCT/EP00/03210

§ 371 (c)(1),
(2), (4) Date: Jan. 9, 2002

(87) PCT Pub. No.: WO00/61124

PCT Pub. Date: Oct. 19, 2000

(30) Foreign Application Priority Data

Apr. 12, 1999 (EP) .............................................. 99106206
Apr. 29, 1999 (EP) .............................................. 99107474

(51) Int. Cl.[7] .............................................. A61K 31/40
(52) U.S. Cl. ...................................................... 514/414
(58) Field of Search ......................................... 514/414

(56) References Cited

U.S. PATENT DOCUMENTS 5,935,581 A * 8/1999 Kapadia et al. .......... 424/195.1

FOREIGN PATENT DOCUMENTS

WO    WO 99/62503    12/1999
WO    WO 00/61555    10/2000

OTHER PUBLICATIONS

Li et al., Chung Hua I Hsueh Tsa Chih, (1979), 59, (3), 129–132 Abstract.*
Dyer, AN index of Tumor chemotherapy, NIH, Mar. 1949, pp. 10–12 and 131.*
International Search Report (For PCT/ISA/210), PCT/EP00/03210.
Derwent, database WPI, XP 002164029 abstract for JP 61 007254 A, Jan. 13, 1986.
Derwent, database WPI, XP 002164030 abstract for JP 57 209271 A, Dec. 22, 1982.
Derwent, database WPI, XP 002164031 abstract for 57 209272 A, Dec. 22, 1982.
Derwent, database WPI, XP 002164032 abstract for CN 1 207 924 A, Feb. 17, 1999.
K.C. Tsou et al., "Indigogenic Phosphodiesters as Potential Chromogenic Cancer Chemotherapeutic Agents," J. Med. Chem. 1972, vol. 15, No. 12, pp. 1221–1225.
Kemei Wu et al., "Potential Antileukemic Agents, Synthesis of Derivatives of Indirubin, Indigo, Isoindigotin, " Act Pharmaceutica Sinica, 1985, vol. 20, No. 11, pp. 821–826.
L. Li et al., "Chemical Studies of Strobilanthes cusia, "Acta Pharmaceutica Sinica, 1993 vol. 28, No. 3, pp. 238–240.

* cited by examiner

*Primary Examiner*—Jerome D. Goldberg
(74) *Attorney, Agent, or Firm*—Burns, Doane, Swecker & Mathis, L.L.P.

(57) ABSTRACT

The present invention relates to the use of cell membrane penetrating indigoid bisindole derivatives for the manufacture of a medicament for the treatment of human solid cancers.

5 Claims, 8 Drawing Sheets

USE OF CELL MEMBRANE PENETRATING INDIGOID BISINDOLE DERIVATIVES

This application is a 371 of PCT/EP00/03210 filed Apr. 11, 2000.

The present invention relates to the use of cell membrane penetrating indigoid bisindole derivatives for the manufacture of a medicament for the treatment of human solid cancers.

Indigoid bisindoles comprise a spectrum of natural dye stuffs. Many of these can be obtained from plants. Accordingly, indirubin, indigo and isoindigo are natural products which can be obtained from different plants: namely, *Baphicacanthus cusia* (Acanthaceae), *Indigofera suffruticosa* (Fabaceae), *Isatis indigotica* (Brassicaceae) and others. Indican, a glycoside which is found in plants, gives glucose and 3-hydroxyindole due to acidic or enzymatic hydrolysis. 3-Hydroxy-indole is converted by air-oxidation into indigo and its isomers. Indigo naturalis (Chinese: quingdai) is the natural blue dye obtained from plant material, e.g. *Isatis indigotica* (Brassicaceae). Indirubin, an isomer of indigo, can be found in Indigo naturalis in an amount of up to 60% (Falbe J. & Regitz M., Römpp Chemie Lexikon (1992), 9. Aufl., Stuttgart, Georg Thieme Verlag). It occurs also in *Isatis tinctoria* in an amount of up to 5% which is indigenous to Central Europe (Gelius R., Z. Chem., 20, (1980), 340–341). Derivatives of indirubin are known for a long time as dyes of low persistence.

Indigo naturalis is reported to be used in traditional Chinese medicine as a haemostatic, anti-pyretic, anti-inflammatory and sedative agent in the treatment of bacterial and viral infections. Antileukemic effects of Indigo naturalis have also been reported, with indirubin being the effective principle (Ji X. et al., Acta Pharm. Sin., 16, (1981), 146–148; Gan W. J. et al., J. Hematol., 6, (1985), 611–613). In spite of its anti-leukaemic activity, however, indirubin dissolves only poorly in water and is therefore not readily resorbed. Recently, the antileukemic activity of some better soluble indirubin derivatives has been reported (Ch. Li et a., Bull. Chem. Soc. Jpn. 69, 1621–1627 (1996)).

However, indigoid bisindole or its derivatives have never been investigated with respect to solid tumors, in particular human solid tumors, and furthermore, the problem of the poor solubility resulting in a poor resorption has not been sufficiently solved yet.

Thus, the technical problem underlying the present invention is to provide new active substances which can be used in the treatment of human solid tumors and metastasis thereof. Furthermore, the resorption of said substances should be improved in order to improve their in vivo anti-tumor activity.

The solution to the above technical problem is achieved by the embodiments characterized in the claims.

In particular, the present invention relates to the use of cell membrane penetrating indigoid bisindole derivatives for the manufacture of a medicament for the treatment of human solid tumors and metastasis thereof wherein the indigoid derivatives are selected from indigo, bis(3-phenylindol-2-yl), isoindigo and indirubin derivatives, the latter represented by the following formula (I):

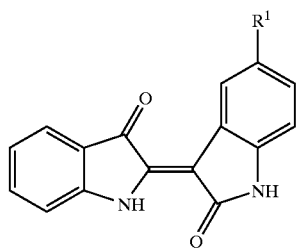

wherein, when X represents an oxygen atom, $R^1$ represents a hydrogen atom, a halogen atom, a —$NO_2$ group, a methyl group, a sulfonamide group or $SO_2$—NH—$CH_2CH_2$—OH; and wherein, when X represents NOH, $R^1$ represents a hydrogen atom or an iodine atom.

The above indigoid bisindole derivatives can also be employed in the form of their physiologically acceptable salts. Furthermore, the indigoid bisindole derivatives according to the present invention may also be chemically coupled to masking agents as described e.g. in German patent application DE-A-38 27 488 which function to carry the anti-tumor active substances to the tumor.

In the following, the indigoid derivatives selected from indigo, isoindigo and indirubin derivatives according to the present invention are also addressed to as "anti-tumor active compounds according to the present invention".

According to the present invention the terms "cell membrane penetrating" and "cell resorbable" mean the ability of the indigoid bisindole derivatives to be taken up by the tumor cell through the cellular membrane.

The term "human solid tumors" according to the present invention preferably includes carcinomas, melanomas, adenomas, sarcomas, lymphomas, neuroblastomas, teratomas, astrocytomas, glioblastomas and mesotheliomas. Specific examples are mammary carcinoma, large-cell lung carcinoma, small-cell lung carcinoma, lung epidermoid and adenocarcinoma, colorectal carcinoma, bladder carcinoma, ovarian carcinoma, pancreatic carcinoma, renal carcinoma, prostatic carcinoma, head and neck carcinomas, melanomas, cervical carcinomas, osteosarcoma and the like.

The above identified indigoid bisindole derivatives of the present invention can be formulated into pharmaceutical compositions which contain optionally a pharmaceutically acceptable carrier and/or diluent. Said pharmaceutical compositions can be applied e.g. orally, topically, intravenously, intraperitoneally, subcutaneously and rectally in pharmaceutically effective amounts.

One general problem in the field of pharmacology is the formulation of pharmaceutically active substances in pharmaceutical compositions which can be applied to a human body. Since most physiological fluids are waterbased, the pharmaceutically active substances should be soluble in water and/or a water mixable solvent wherein the latter of course has to be physiologically acceptable in small concentrations, such as ethanol. Furthermore, pharmaceutically active substances which are taken orally have to be resorbed into surface of the human body—including the gastrointestinal mucous membrane—or, in case of an application via syringe, e.g. intraperitoneal or intravasal, have to be resorbed through the cellular membranes of the of destination cells, specifically into the tumor cells.

According to the present invention it has been found that in case of the indigoid bisindole derivatives according to the present invention, a good solubility is not the only prerequisite guaranteeing a good anti-tumor activity in viva as it will become apparent by the Examples and Comparative Examples shown below. An important factor for the anti-tumor activity of indigoid bisindole derivatives is their ability to penetrate the cellular membranes of the tumor cells. Cellular membranes are composed of lipids and compose a rather non-polar medium. Therefore, substitution with extremely polar groups such as the sulfonate group on the one hand improves the water solubility of a compound but on the other hand hinders or even prohibits the resorption of anti-tumor active substances into a tumor cell. Thus, anti-tumor active substances which show good anti-tumor activities under certain in vitro conditions, have to be rejected because of not showing any activity when tested using intact cells or in vivo.

Therefore, in the following Examples the testing of the anti-tumor active substances are tested by in vitro tests using intact tumor cells and, additionally, in vivo tests. Furthermore, a comparison of the activity test results and the tests evaluating the ability to penetrate cellular membranes shows that indigoid bisindole compounds which exhibit a good cell-penetrating ability also show good to excellent anti-tumor activity.

THE FIGURES SHOW:

FIG. 1 is a graph which shows the development of the relative tumor volume with time during chemotherapy of LXFL 529/17 with indigoid bisindole derivatives according to the present invention (compounds according to Examples 1, 4 and 6). The anti-tumor active substances according to the present invention were applied intraperitoneally to nude mice in doses and according to the schedule as described below in Table 4. Compared to the vehicle control, all compounds significantly inhibited the tumor growth.

FIG. 2 is a graph which shows the relative body weight change of the tested nude mice with time during chemotherapy of LXFL 529/17. 5-Methylindirubin (Example 6) at a dosage of 100 mg/kg up to 300 mg/kg showed very high anti-tumor activity (FIG. 1 and FIG. 3) without any significant reduction of body weight (FIG. 2 and FIG. 4) thus demonstrating high anti-tumor activity without significant toxicity.

Figure 1:
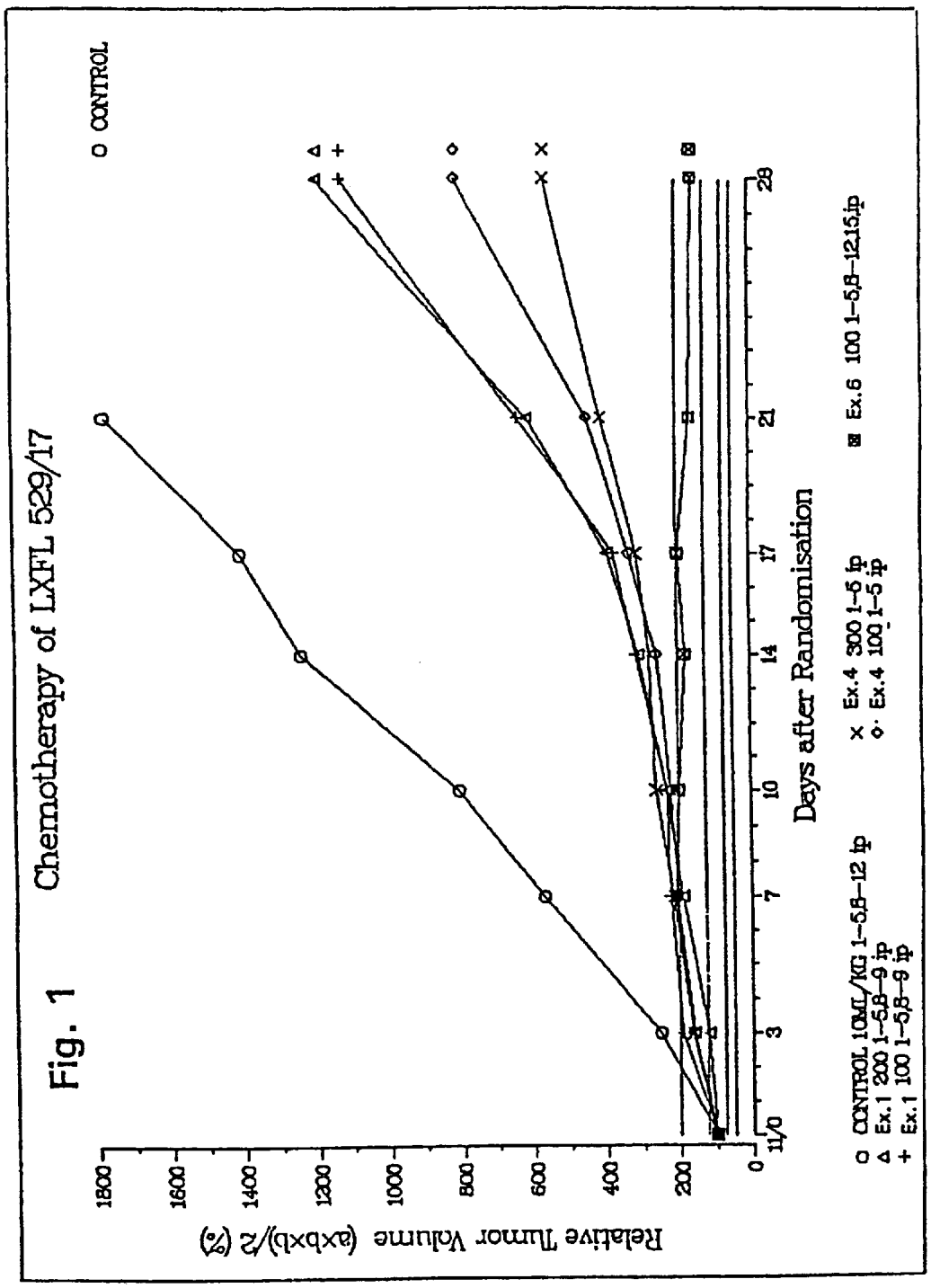

The present invention is explained in detail by the following examples and comparative examples by which also further advantages of the present invention will become apparent.

1. SYNTHESIS OF THE INDIGOID BISINDOLE DERIVATIVES

EXAMPLE 1

Indirubin

To a solution of 0.42 g (2.4 mmol) of indoxyl acetate in 20 ml methanol under argon 0.35 g (2.4 mmol) of satin and 0.55 g (5.2 mmol) of sodium carbonate are added. The mixture is stirred for 30 min at ambient temperature. After 24 h standing at ambient temperature, the reaction mixture is filtered off. The precipitate is washed with little methanol and water until the filtrate shows a neutral pH. Residual water is removed by storage in an evacuated exsiccator over potassium hydroxide. Recrystallisation from ethanol or pyridine gives deep purple crystals (Russell G. A., Kaupp G. (1969), J. Am. Chem. Soc., 91, 3851–9, modified).

Yield: 0.51 g (81%), fine, deep-purple needles, Fp: 341–343° C.; CHN-analysis: ($C_{16}H_{10}N_2O_2$); MW: 262.26 g/mol; calc.: 73.3% C, 3.8% H, 10.7% N; found: 73.2% C, 4.0% H, 10.6% N; mass spectrum: m/z=262: ($M^+$, 100%), 234: (43%), 205 (25%), 158 (3%), 131 (4%), 103 (7%), 76 (3%); $^1$H-NMR and $^{13}$C-NMR-spectrum are in accordance with the proposed structure. IR-spectrum: $3340 cm^{-1}$: v (N—H), $1710\ cm^{-1}$: v (3'—C=O), $1650\ cm^{-1}$: v (2—C=O), $1590\ cm^{-1}$: v (C=C, aryl), $1450\ cm^{-1}$: v (C=C, aryl), $745\ cm^{-1}$: v (aryl with four neighbouring H-atoms). UV/Vis-spectrum (DMSO): 290 nm, 363 nm, 383 nm (shoulder), 551 nm.

Essentially the same synthetic procedure was applied for the following Examples 2 to 9, 12, 13 and Comparative Examples 1 and 2:

EXAMPLE 2

5-Lodoindirubine

Yield: 80%, fine, deep-purple needles, Fp: 334–335° C. (decomposition); CHN-analysis ($C_{16}H_9IN_2O_2$); MG=388.16 g/mol; calc.: 49.5% C, 2.3% H, 7.2% N; found.: 49.7% C, 2.5% H, 7.1% N; Mass spectrum: 388 ($M^+$, 100%), 360 (3%), 269 (9%), 261 (6%), 233 (16%), 205 (16%), 128 (1%); $^1$H-NMR- and $^{13}$C-NMR-spectrum are in accordance with the proposed structure. UV/Vis-spectrum (DMSO): 370 nm, 386 nm (shoulder), 555 nm.

EXAMPLE 3

5-Bromoindirubin

Yield: 70%, fine, deep-purple needles; CHN-analysis ($C_{16}H_9BrN_2O_2$); MG=341.16 g/mol, calc.: 56.3% C, 2.7% H, 8.2% N; found 56.4% C, 2.7% H, 8.2% N; Mass spectrum: 342($M^+$, 100%), 340 ($M^+$, 99%), 314 (18%), 262 (64%), 233 (34%), 205 (81%), 177 (10%); $^1$H-NMR- and $^{13}$C-NMR-spectrum are in accordance with the proposed structure.

EXAMPLE 4

5-Chloroindirubin

Yield: 95%, fine, deep-purple needles; CHN-analysis ($C_{16}H_9CIN_2O_2$); MG=296.70 g/mol; calc.: 49.5% C, 2.3% H, 7.2% N; found: 49.7% C, 2.5% H, 7.1 % N; Mass spectrum: m/z=296 ($M^+$, 100%), 268 (39%), 239 (8%), 233 (35%), 205 (50%), 177 (7%), 153 (6%), 137 (7%), 77 (7%), 120 (4%), 102 (6%), 77 (7%). $^1$H-NMR- and $^{13}$C-NMR-spectrum are in accordance with the proposed structure.

EXAMPLE 5

5-Fluoroindirubin

Yield: 92%, fine, deep-purple needles; CHN-analysis ($C_{16}H_9FN_2O_2$), MG=280.25 g/mol, calc.: 68.6% C, 3.2% H, 9.9% N; found: 68.0% C, 3.2% H, 9.9% N; Mass spectrum: m/z=281 ($M^++H^+$, 19%), 280 ($M^+$, 100%), 252 (73%), 223 (32%), 176 (6%), 140 (7%), 121 (13%), 94 (4%), 76 (12%), 77 (7%), 57 (4%), 44(15%). $^1$H-NMR- and $^{13}$C-NMR-spectrum are in accordance with the proposed structure.

EXAMPLE 6

5-Methylindirubin

Yield: 92%, fine, deep-purple needles; CHN-analysis ($C_{17}H_{12}N_2O_2$), MG=276.28 g/mol, calc.: 73.9% C, 4.4% H, 10.1% N; found: 73.8% C, 4.3% H, 10.2% N; Mass spectrum: m/z=276 (M$^+$, 100%), 261 (10%), 248 (47%), 247 (53%), 220 (6%), 219 (18%), 205 (7%), 171 (4%), 165 (10%), 138 (4%), 133 (15%), 104 (7%), 77 (7%); $^1$H-NMR- and $^{13}$C-NMR-spectrum are in accordance with the proposed structure.

EXAMPLE 7

5-Nitroindirubin

Yield: 88%, fine, deep-purple needles; CHN-analysis ($C_{16}H_9N_3O_4$), MG=307.26 g/mol; calc.: 62.5% C, 3.0% H, 13.7% N; found: 62.4% C, 3.0% H, 13.3% N; Mass spectrum: m/z=307 (M$^+$, 5%), 276 (10%), 262 (100%), 234 (23%), 205 (22%), 158 (6%), 131 (10), 104 (19%), 76 (12%), 50 (6%). $^1$H-NMR- and $^{13}$C-NMR-spectrum are in accordance with the proposed structure.

EXAMPLE 8

Indirubin-3'-oxime

Indirubin-3'-oxime was synthesized by reaction of indirubin with hydroxylamine hydrochloride in a pyridine solution (Farbwerke vorm. Meister Lucius & Brüning in Hoechst a.M., Patentschrift des Reichspatentamtes Nr. 283726 (1913)). $^{13}$C-NMR-spectroscopy revealed the location of the hydroxyimino residue in 3'-Position ($\delta$(C2)=171.05 ppm; $\delta$(C3')=145.42 ppm; DMSO-d$_6$, RT).

Yield: 90%, red crystals; CHN-analysis ($C_{16}H_{11}N_3O_2$), MG=277.30 g/mol; calc.: 69.3% C, 4.0% H, 15.2% N; found: 69.0% C, 4.0% H, 14.9% N; $^1$H-NMR- and $^{13}$C-NMR-spectrum are in accordance with the proposed structure.

EXAMPLE 9

5-Lodoindirubine-3'-oxime

Indirubin-3'-oxime was synthesized by reaction of 5-Lodoindirubine with hydroxylamine hydrochloride in a pyridine solution. $^{13}$C-NMR-spectroscopy revealed the location of the hydroxyimino residue in 3'-Position ($\delta$(C2)= 170.25 ppm; $\delta$(C3')=151.52 ppm; DMSO-d$_6$, RT).

Yield: 90 %, red crystals; CHN-analysis ($C_{16}H_{10}IN_3O_2$), MG=403,20 g/mol; calc.: 47.7% C, 2.5% H, 10.4% N; found: 47.1% C, 2.5% H, 10.1% N; $^1$H-NMR- and $^{13}$C-NMR-spectrum are in accordance with the proposed structure.

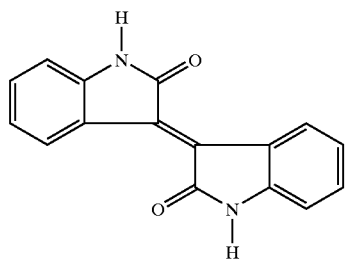

EXAMPLE 10

Isoindigo

Isoindigo was synthesized by reaction of oxindole with isatin in acetic acid with addition of hydrochloric acid (Wahl A., Bayard P., Comptes Rendues Hebdomadaires des Seances de L'Academie des Sciences, 148, (1909), 716–719).

Yield: 84%, crystalline, brown substance; CHN-analysis ($C_{16}H_{10}N_2O_2$), MG=262.26 g/mol; calc.: 73.3% C, 3.8% H, 10.7% N; found: 73.0% C, 3.8% H, 10.9% N; Mass spectrum: m/z=262 (M$^+$, 100%), 234 (85%), 220 (5%), 205 (18%), 190 (4%), 177 (5%), 151 (5%), 132 (17%), 103 (6%), 76 (4%), 32 (26%). $^1$H-NMR- and $^{13}$C-NMR-spectrum are in accordance with the proposed structure.

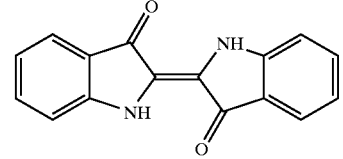

EXAMPLE 11

Indigo

Chemical grade indigo was purchased by Fluka Chemie AG.

EXAMPLE 12

Indirubin-5-sulfonamide $^1$H-NMR- and $^{13}$C-NMR-spectrum are in accordance with the proposed structure.

EXAMPLE 13

Indirubin-5-Sulfone(2-hydroxyethyl)amide $^1$H-NMR- and $^{13}$C-NMR-spectrum are in accordance with the proposed structure.

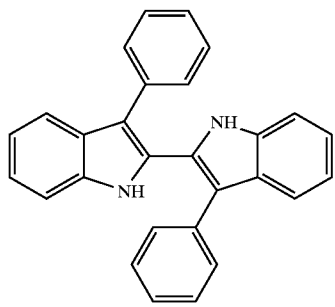

EXAMPLE 14

Bis(3-Phenylindol-2-yl)

To a cooled solution of 2-aminobenzophenone in dichloromethane and pyridine under inert gas, a solution of oxalyl chloride in dichloromethane is dropped. After completion of the reaction, 0.5 n hydrochloric acid is added, the formed precipitate is filtrated off and washed subsequently with 0.5 n hydrochloric acid, a solution of sodium hydrogencarbonate and water. The obtained product (N,N'-bis(2-benzoylphenyl)-oxamide), zinc dust and titanium(III) chloride are suspended in dimethoxyethane and heated to reflux. After heating for 3 h, the mixture is cooled to ambient temperature and the precipitate is filtrated off and washed with ethyl acetate. The crude product is purified using column chromatography (silica gel), then dissolved in ethyl acetate and precipitated in form of white crystals by adding petrol ether.

CHN-analysis ($C_{28}H_{20}N_2$), MG=384.48 g/mol; calc.: 87.5% C, 5.2% H, 7.3% N; found: 87.3% C, 5.3% H, 7.3% N; $^1$H-NMR- and $^{13}$C-NMR-spectrum are in accordance with the proposed structure.

COMPARATIVE EXAMPLE 1

Indirubin-5-sulfonic Acid

Yield: 76%, crystalline, deep-purple substance; Mass spectrum: 388 (M$^+$, 100%), 360 (3%), 269 (9%), 261 (6%), 233 (16%), 205 (16%), 128 (1%). $^1$H-NMR- and $^{13}$C-NMR-spectrum are in accordance with the proposed structure.

COMPARATIVE EXAMPLE 2

Indirubin-3'-oxime-5-sulfonic acid

Yield: 76%, crystalline, deep-purple substance; Mass spectrum: 388 (M$^+$, 100%), 360 (3%), 269 (9%), 261 (6%), 233 (16%), 205 (16%), 128 (1%). $^1$H-NMR- and $^{13}$C-NMR-spectrum are in accordance with the proposed structure.

Table 2 summarizes the structures of the indirubin compounds of Examples 1 to 9 and Comparative Examples 1 and 2.

TABLE 1

| | compound | R$^1$ | X |
|---|---|---|---|
| Example | | | |
| 1 | Indirubin | H | O |
| 2 | 5-Iodoindirubin | I | O |
| 3 | 5-Bromoindirubin | Br | O |
| 4 | 5-Chloroindirubin | Cl | O |
| 5 | 5-Fluoroindirubin | F | O |
| 6 | 5-Methylindirubin | CH$_3$ | O |
| 7 | 5-Nitroindirubin | NO$_2$ | O |
| 8 | Indirubin-3'-oxime | H | NOH |
| 9 | 5-Iodoindirubine-3'-oxime | I | NOH |
| 10 | Isoindigo | | |
| 11 | Indigo | | |
| 12 | Indirubin-5-sulfonamide | SO$_2$—NH$_2$ | O |
| 13 | Indirubin-5-sulfone(2-hydroxyethyl)amide | SO$_2$—NH—CH$_2$CH$_2$OH | O |
| 14 | Bis(3-phenylindol-2-yl) | | |
| Comparative Examples | | | |
| 1 | Indirubin-5-sulfonic acid | SO$_3$H | O |
| 2 | Indirubin-3'-oxime-5-sulfonic acid | SO$_3$H | NOH |

2. CELLULAR UPTAKE INTO LXFL 529L CELLS

The compounds of Examples 1, 6 and 8 and Comparative Examples 1 and 2 were investigated with respect to their ability to penetrate LXFL 529L cells having the passage numbers P23 to P39. The results are shown in Table 2. The amounts of the substances taken up by the cells are given depending on the concentration of the substance within the incubation medium. The time of incubation was 2 hours in all of the experiments. Furthermore, the distribution of the substance which was taken up by the cells in the cytosol and the cellular organelles (particular) was estimated and is given in the intermediate column of Table 2. Tumor cell growth inhibition was determined by the sulfo-rhodamine B assay (SRB assay) according to Skehan et al., *J. Natl. Cancer Institute* 82, pages 1107–1112 (1990). Incubation was conducted for three days in serum containing medium. Tumor cell lines tested were a large-cell lung carcinoma xenograft line LXFL 529 L and the mammary carcinoma line MCF-7. Results are given as $IC_{50}$ [$\mu$M] corresponding to the concentration of compounds inducing 50% growth inhibition, compared to vehicle treated control.

clonongenic assay with human tumor xenografts, evaluation, predictive values and application for drug screening".

The experiments were conducted using various tumor cell lines, in particular mammary carcinoma (MAXF), lung adenocarcinoma (LXFA), large-cell lung carcinoma (LXFL), small-cell lung carcinoma (LXFS), colon carcinoma (CXF), melanoma (MEXF), pancreatic carcinoma (PAXF), renal carcinoma (RXF), ovarian carcinoma (OVXF) and bladder carcinoma (BXF).

The $IC_{70}$-values and $IC_{50}$-values, respectively, define the concentration of a pharmaceutically active compound causing 70% and 50%, respectively, reduction of colony formation compared to the untreated control. Therefore, $IC_{70}$- and IC50-values serve to demonstrate the anti-tumor activity of a pharmaceutically active compound wherein low $IC_{70}$- and/or $IC_{50}$-values demonstrate a superior anti-tumor activ-

TABLE 2

| substance | concentration of incubation [$\mu$M] | amount of substance within the cells [$\mu$m/mg protein] | distribution [%] cytosol | distribution [%] organelles | Tumor cell growth inhibition (SRB-assay) $IC_{50}$ [$\mu$M] LXFL529L | Tumor cell growth inhibition (SRB-assay) $IC_{50}$ [$\mu$M] MCF7 |
|---|---|---|---|---|---|---|
| Example 1 | 10 | 0.15 ± 0.08 | 7 ± 5.7 | 93 ± 5.7 | 9.9 ± 0.1 | 4.0 ± 2.0 |
|  | 20 | 0.20 ± 0.08 | 6 ± 1.4 | 94 ± 1.4 |  |  |
| Example 6 | 10 | 0.52 ± 0.1 | 13 ± 0.7 | 87 ± 0.7 | 7.5 ± 0.5 | 4.8 ± 0.5 |
|  | 20 | 0.86 ± 0.22 | 6 ± 2.8 | 94 ± 2.8 |  |  |
| Example 8 | 10 | 0.16 ± 0.01 | 43 ± 14.1 | 57 ± 14.1 | 3.0 ± 0.5 | 3.3 ± 0.4 |
|  | 20 | 0.23 ± 0.03 | 44 ± 15.6 | 56 ± 15.6 |  |  |
| Comparative Example 1 | 10 | <0.02 | — | — | >100 | >100 |
|  | 20 | <0.02 | — | — |  |  |
| Comparative Example 2 | 10 | <0.05 | — | — | >100 | >100 |
|  | 20 | <0.05 | — | — |  |  |

The compounds according to the Examples 1, 6 and 8 were all taken up by the tumor cells. The ability of the compound according to Example 6 to penetrate the cellular membrane is substantially improved compared to that of the parent compound indirubin (Example 1). The uptake of the compound according to Example 8 is also slightly improved compared to the non-substituted indirubin (Example 1).

The compounds of Comparative Examples 1 and 2 were essentially not taken up by the cells although these compound are well soluble in physiological solutions. Obviously, the sulfonate group hinders the penetration through the cellular membrane. Furthermore, referring to Comparative Example 2, this detrimental effect cannot be compensated by the introduction of an oxime group.

3. EVALUATION OF THE ANTI-TUMOR ACTIVITY

The anti-tumor activity of the compounds was evaluated via a colony-forming-assay as described e.g. by D. P. Berger et al. in *Annals of Oncology* 1, pages 333–341 (1 990), "The ity. According to the present invention, the $IC_{70}$-value preferably is 20 $\mu$M or lower, more preferably 10 $\mu$M or lower.

Table 3 shows the anti-tumor activity of the compounds according to the Examples and Comparative Example 1. The compounds according to the inventive Examples show good to excellent anti-tumor activity against various types of tumor cell lines. The compound according to Comparative Example 1 does not exhibit an anti-tumor activity against any of the tumor lines. This behavior is in accordance with the lacking ability of this substance to penetrate cellular membranes as demonstrated in Table 2, above.

Surprisingly, small variations in the substitution pattern result in remarkable changes in the anti-tumor activity profile. However, almost all compounds according to the Examples exhibit good anti-tumor activity against mammary carcinoma.

TABLE 3

| Example | IC$_{50}$ [μM] | IC$_{70}$ [μM] | tumor xenograft type | xenograft |
|---|---|---|---|---|
| 1 (indirubin) | 25.3 | 35.6 | lung large-cell | LXFL529 |
| | 2.0 | 6.0 | mammary | MCF7X |
| | 12.3 | >30 | ovarian | OVXF1353 |
| | 5.4 | >30 | pancreatic | PAXF736 |
| 2 (5-iodo-indirubin) | 6.3 | >30 | colon | HT29X |
| | 8.0 | 23 | lung adeno carcinoma | LXFA526 |
| | 13.7 | 24.5 | lung small-cell | LXFS650 |
| | <1.0 | 2.5 | mammary | MCF7X |
| | 18.0 | >30 | pancreatic | PAXF546 |
| 3 (5-bromo-indirubin) | <1.0 | 17.3 | colon | HT29X |
| | 2.3 | 14.4 | lung adenocarcinoma | LXFA526 |
| | <1.0 | <1.0 | mammary | MCF7X |
| | 3.4 | 8.0 | melanoma | MEXF514 |
| | 13.2 | >30 | pancreatic | HT29X |
| 04 (5-chloro-indirubin) | <1.0 | <1.0 | mammary | MCF7X |
| | 17.1 | 26.0 | melanoma | MEXF514 |
| | 3.2 | 8.0 | pancreatic | PAXF736 |
| | 11.2 | 24.7 | renal | 1220 |
| | 4.6 | >30 | pancreatic | PAXF546 |
| | <1 | 17.3 | colon | HT29X |
| 5 (5-fluoro-indirubin) | <1.0 | <1.0 | mammary | MCF7X |
| | <1.0 | 6.1 | ovarian | OVXF1353 |
| | <1.0 | 1.1 | pancreatic | PAXF736 |
| 6 (5-methyl-indirubin) | <1.0 | 14.4 | colon | HT29X |
| | <1.0 | 1.2 | mammary | MCF7X |
| | 19.2 | 27.8 | melanoma | MEXF514 |
| | 15.4 | 27.5 | pancreatic | PAXF736 |
| | 1.0 | >30 | ovarian | OVXF1352 |
| 7 (5-nitro-indirubin) | <1.0 | 15.1 | mammary | MCF7X |
| | 4.9 | >10.0 | melanoma | MEXF514 |
| 8 (indirubin-3'-oxime) | 10.6 | 16.1 | bladder | BXF1301 |
| | 8.0 | 12.6 | colon | CXF280 |
| | 0.9 | 3.4 | lung adenocarcinoma | LXFA289 |
| | 7.7 | 9.2 | mammary | MX1 |
| | 1.0 | 2.6 | melanoma | MEXF989 |
| | 2.8 | 5.7 | melanoma | MEXF515LX |
| 9 (5-iodo-3'-oxime-indirubin) | 4.0 | 5.8 | bladder | BXF1301 |
| | 10.7 | 16.3 | colon | CXF280 |
| | 0.05 | 0.7 | lung adenocarcinoma | LXFA289 |
| | 2.4 | 10.4 | mammary | MCF7X |
| | 2.6 | 4.9 | melanoma | MEXF515LX |
| 10 (isoindigo) | 6.0 | 8.2 | bladder | BXF1301 |
| | <1.0 | <1.0 | colon | CXF280 |
| | 2.6 | 4.5 | lung large-cell | LXFL529 |
| | <1.0 | <1.0 | lung small cell | LXFS650 |
| | <1.0 | <1.0 | mammary | MX1 |
| | <1.0 | <1.0 | mammary | MCF7X |
| | <1.0 | <1.0 | melanoma | MEXF989 |
| | <1.0 | <1.0 | ovarian | OVXF1355 |
| | <1.0 | <1.0 | pancreatic | PAXF546 |
| | <1.0 | <1.0 | pancreatic | PAXF736 |
| | <1.0 | <1.0 | colon | HT29X |
| 11 (indigo) | 3.3 | 26.1 | colon | HT29X |
| | 3.5 | 12.3 | lung adenocarcinoma | LXFA289 |
| | 3.9 | 16.7 | ovarian | OVXF1353 |
| 13 (5-SO$_2$—NH—CH$_2$—CH$_2$—OH-indirubin) | 12.0 | 17.3 | colon | CXF280 |
| | 1.1 | 2.6 | lung adenocarcinoma | LXFA289 |
| | 3.4 | 5.9 | lung large-cell | LXFL529 |
| | 0.6 | 2.1 | mammary | MCF7X |
| | <0.1 | 0.4 | melanoma | MEXF515LX |
| | 0.3 | 0.4 | ovarian | OVXF899 |
| 14 (Bis(3-phenylindol-2-yl)) | 2.7 | 6.2 | bladder | BXF1299 |
| | <1.0 | 7.2 | colon | CXF280 |
| | 1.6 | 3.4 | colon | HT29X |
| | 4.7 | 6.7 | lung small-cell | LXFS650 |
| | 2.8 | 4.8 | mammary | MX1 |
| Comp. 1 | >30.0 | >30.0 | (all) | |

4. IN VIVO EXPERIMENTS

Compound of Examples 1, 4, 6, 8, 9 and 10 were subjected to in vivo testing in nude mice bearing subcutaneously growing human tumor xenograft LXFL 529. The indigoid bisindole derivatives were applied intraperitoneally to the animals in doses and according to the schedule as described in Table 4.

TABLE 4

Figure 2:
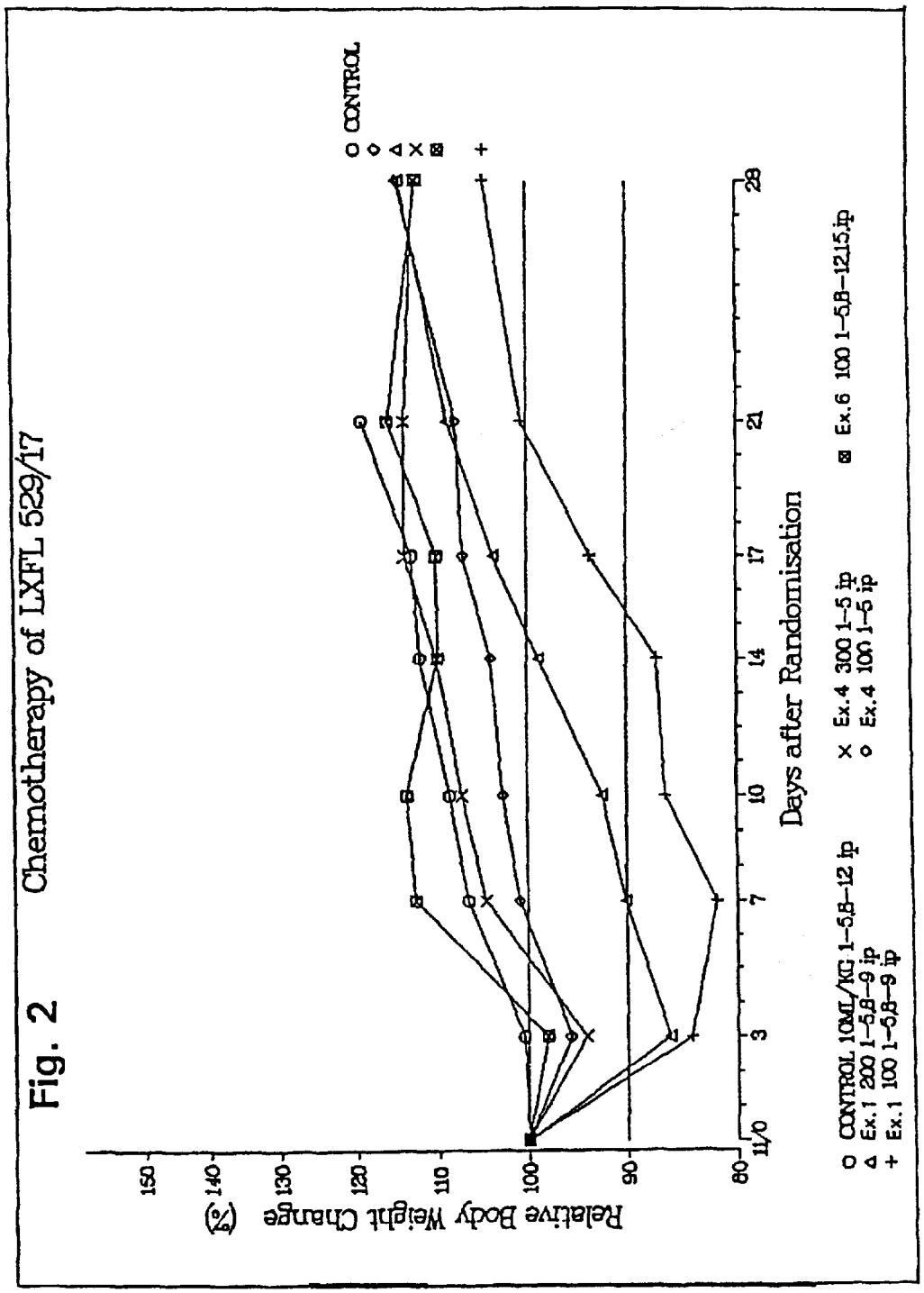
Figure 3:
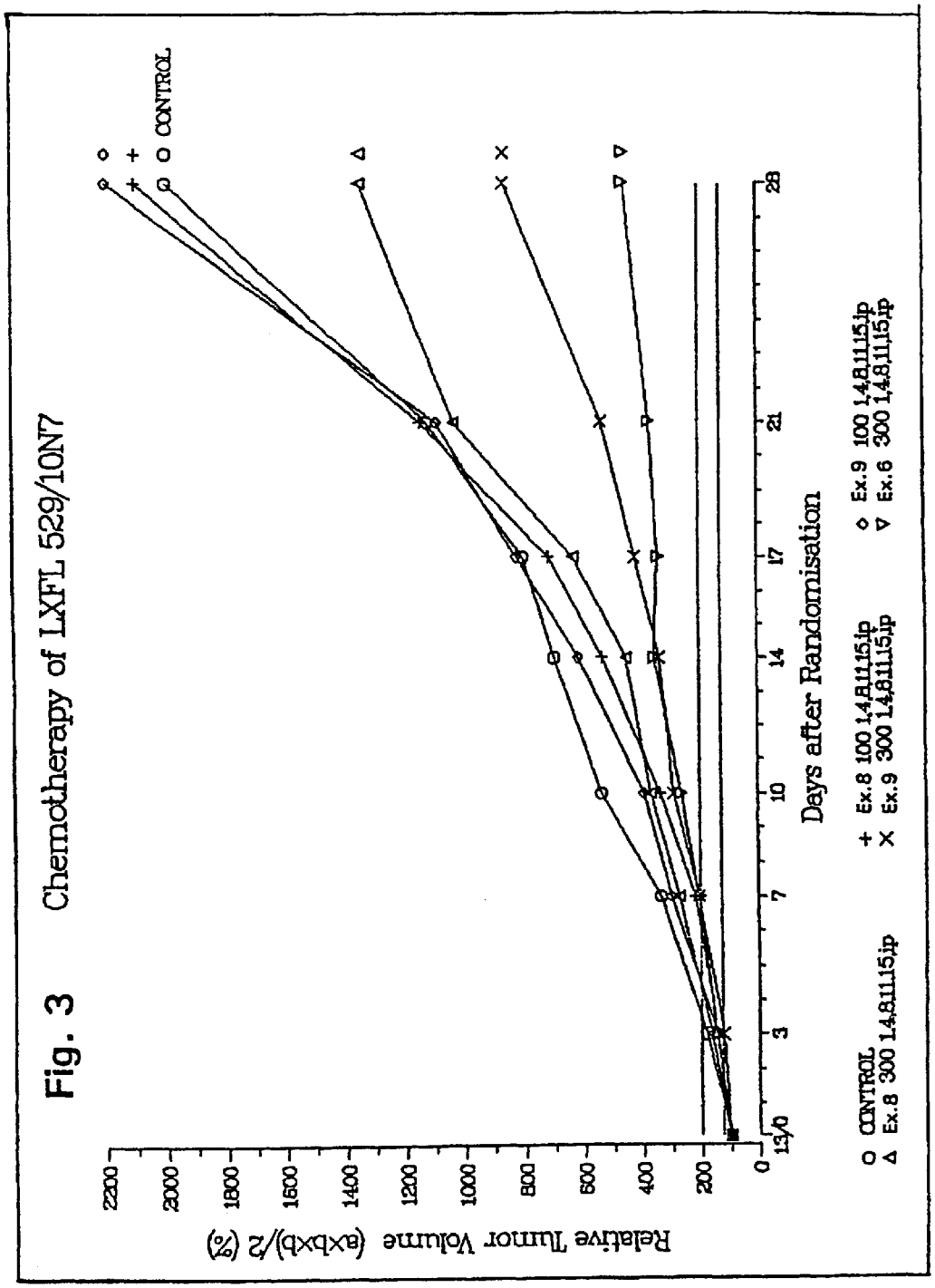
FIG. 3, FIG. 5 and FIG. 7 are graphs which show the relative tumor volume versus the time during the chemotherapy of LXFL 529/17 with other indigoid bisindole derivatives according to the present invention (compounds according to Examples 8, 9, 10 and 14).
Figure 4:
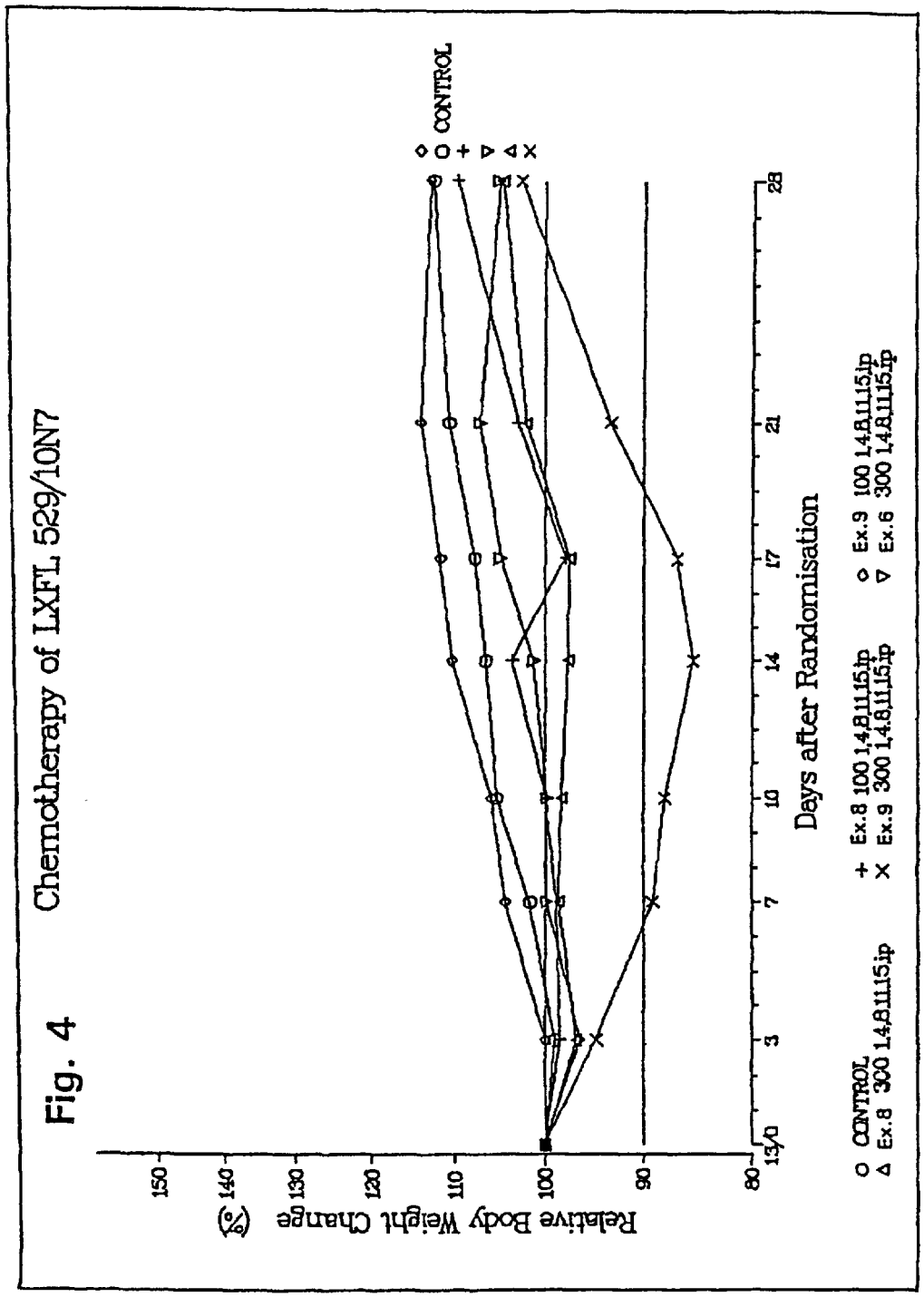
FIG. 4, FIG. 6 and FIG. 8 are graphs which show the relative body weight change of the tested nude mice with time during chemotherapy of LXFL 529/17 using said other indigoid bisindole derivatives according to the present invention.
Figure 5:
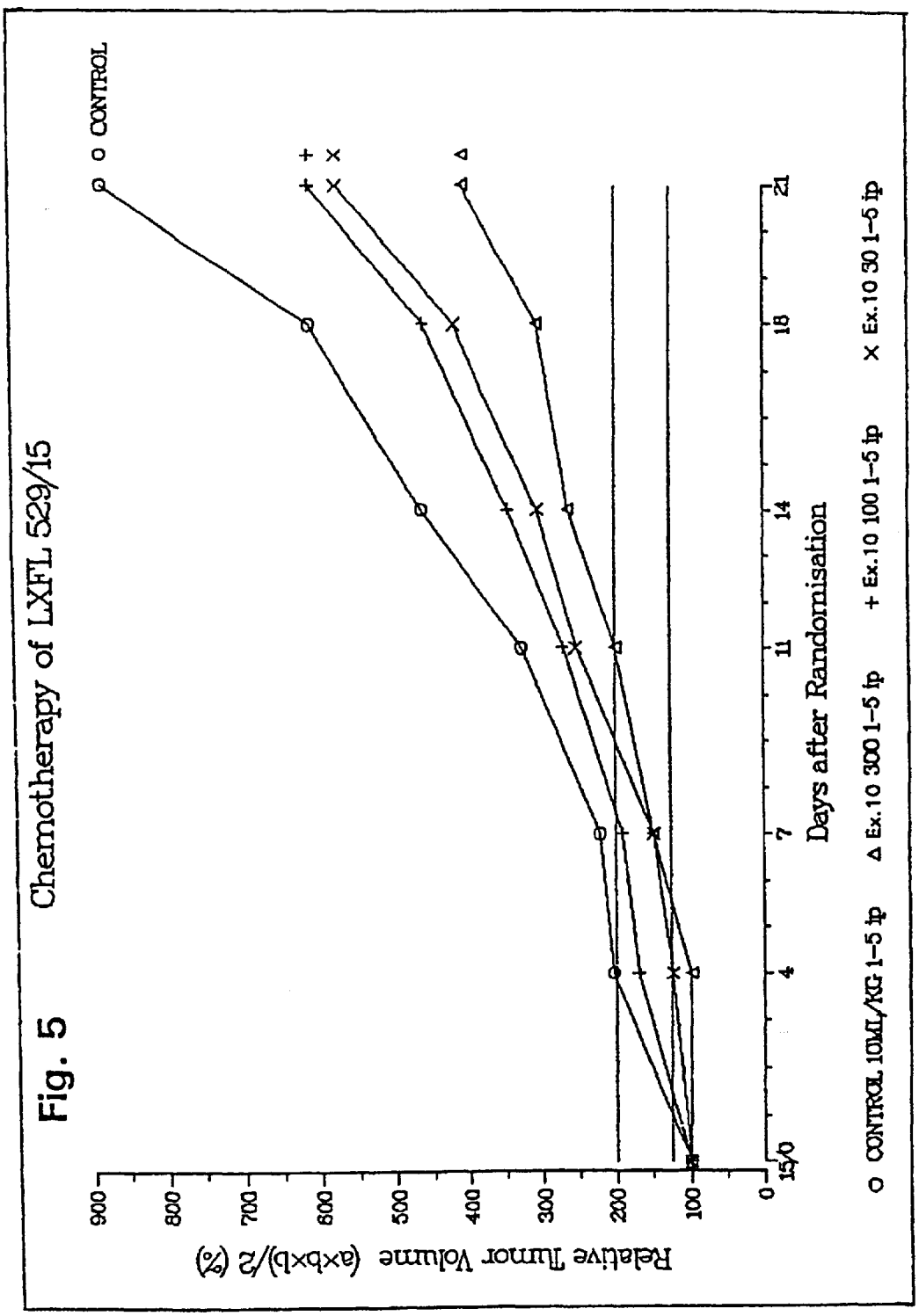
Figure 6:
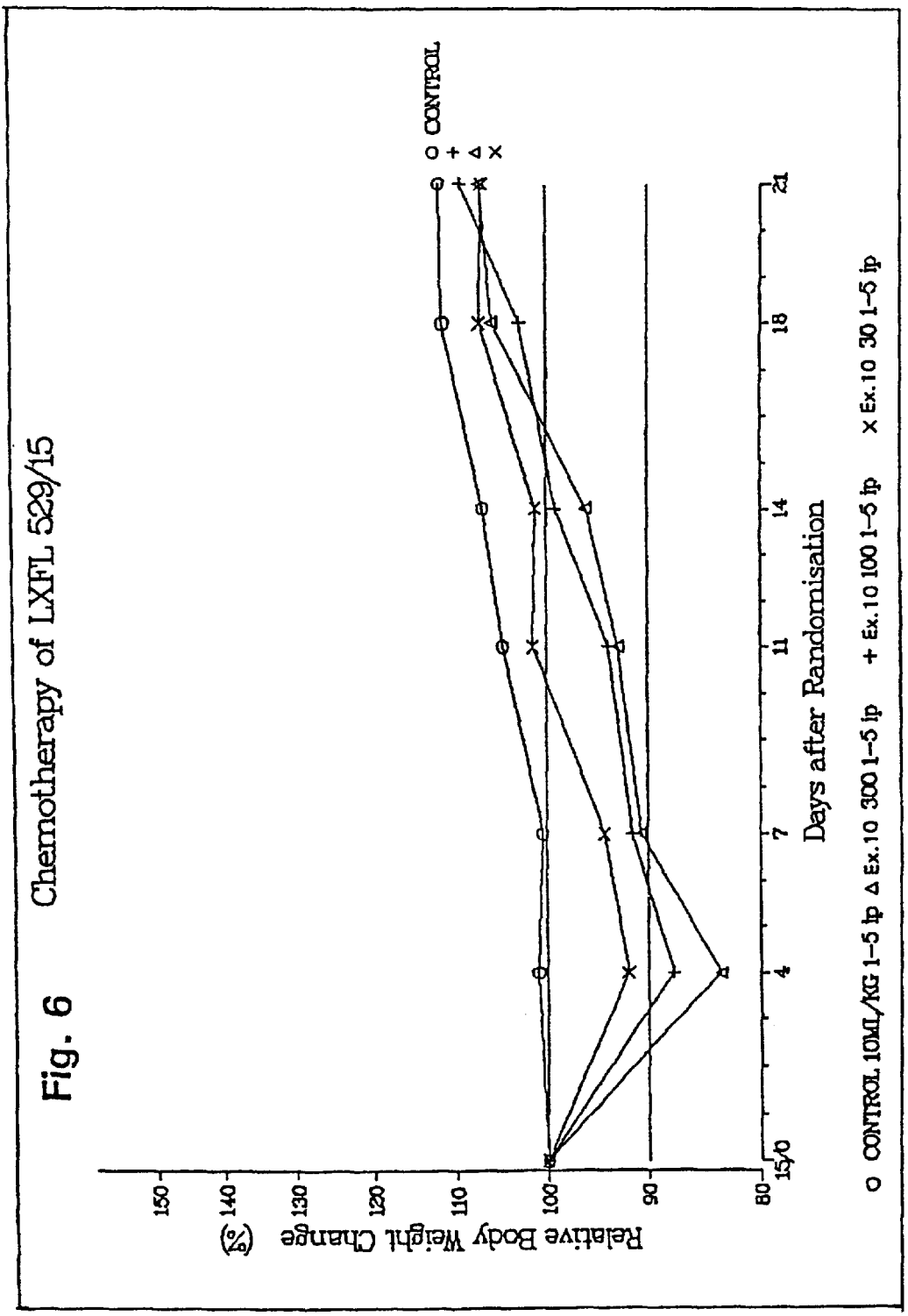
Figure 7:
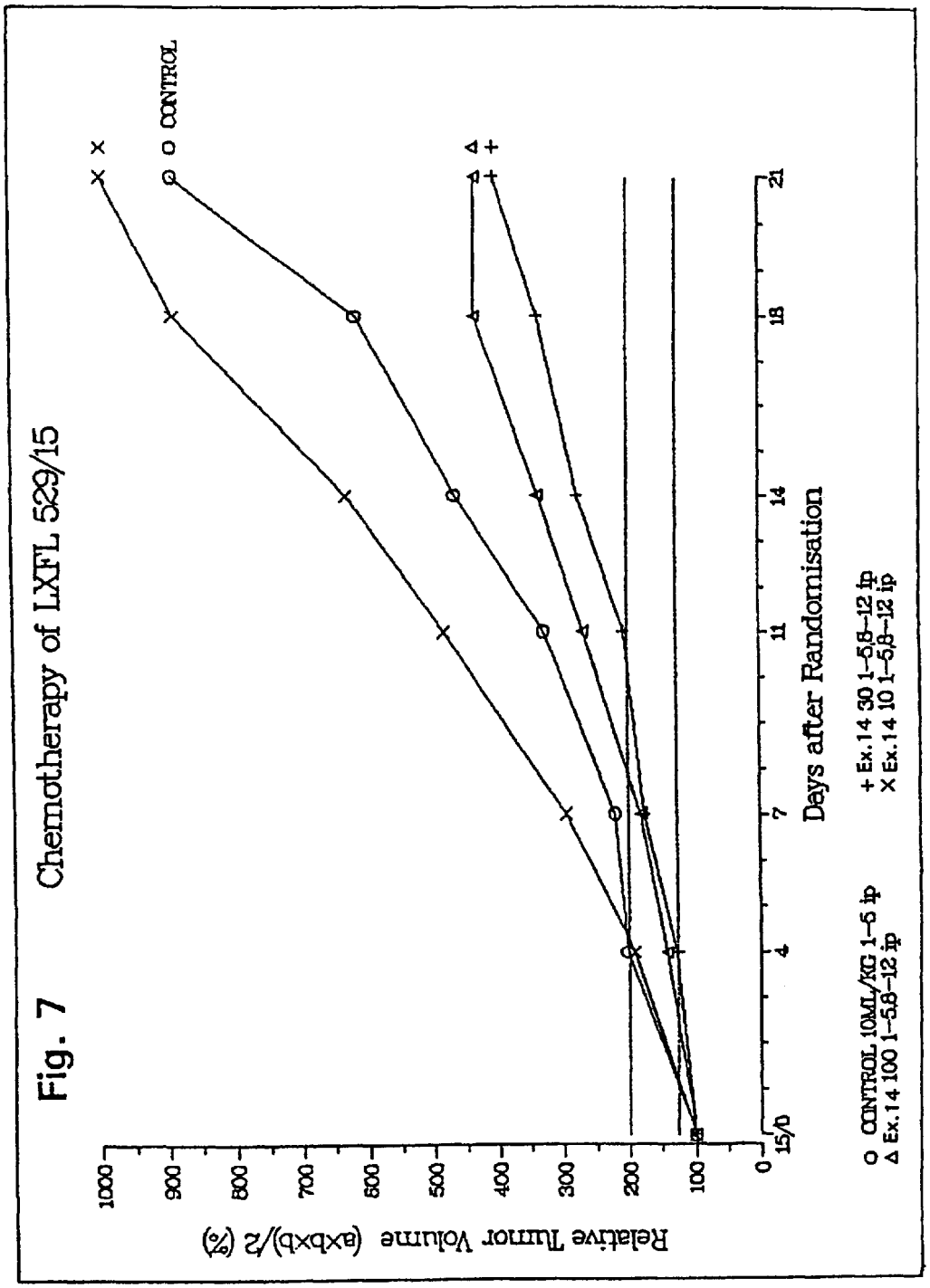
Figure 8:
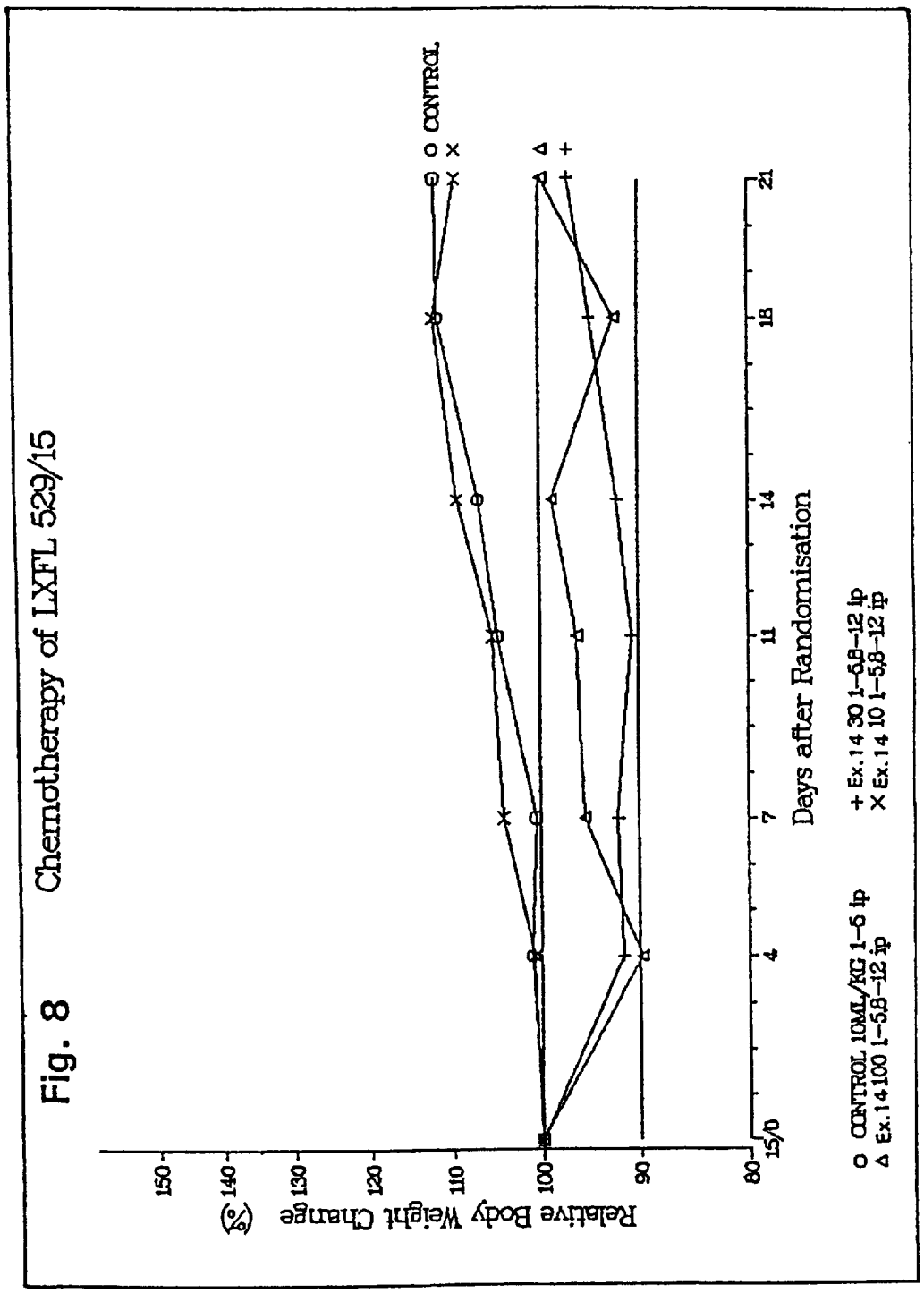

|  | doses [mg/kg/day] | schedule of application [day(s)] | activity rating | Graph shown in Figure |
|---|---|---|---|---|
| Ex. 1 | 100 | 1–5, 8–9 | + | FIG. 1 and 2 |
|  | 200 | 1–5, 8–9 | ++ | FIG. 1 and 2 |
| Ex. 4 | 100 | 1–5 | ++ | FIG. 1 and 2 |
|  | 300 | 1–5 | ++ | FIG. 1 and 2 |
| Ex. 6 | 100 | 1–5, 8–12, 15, 17, 19, 22 | ++ | FIG. 1 and 2 |
|  | 300 | 1, 4, 8, 11, 15, 18, 22 | ++ | FIG. 3 and 4 |
| Ex. 8 | 100 | 1, 4, 8, 11, 15, 18, 22 | − | FIG. 3 and 4 |
|  | 300 | 1, 4, 8, 11, 15, 18, 22 | − | FIG. 3 and 4 |
| Ex. 9 | 100 | 1, 4, 8, 11, 15, 18, 22 | − | FIG. 3 and 4 |
|  | 300 | 1, 4, 8, 11, 15, 18, 22 | + | FIG. 3 and 4 |
| Ex. 10 | 30 | 1–5 | − | FIG. 5 and 6 |
|  | 100 | 1–5 | − | FIG. 5 and 6 |
|  | 300 | 1–5 | + | FIG. 5 and 6 |
| Ex. 14 | 10 | 1–5, 8–12 | − | FIG. 7 and 8 |
|  | 100 | 1–5, 8–12 | + | FIG. 7 and 8 |
|  | 300 | 1–5, 8–12 | + | FIG. 7 and 8 |

The experiments were run for 21 or 28 days. Anti-tumor activity was evaluated comparing the median tumor volume relative to control, expressed as %T/C, wherein T is the test group and C the vehicle control group. In Table 4, anti-tumor activity is given according to an activity rate scale.

| Activity rating: | | |
|---|---|---|
| − | inactive | T/C > 50% |
| + | tumor inhibition | T/C > 25–50% |
| ++ | tumor stasis | T/C ≦ 25% |

The result are further demonstrated by FIGS. 1 to 8.

A reduction of the body weight of the tested mice of more then 20% by weight in general is interpreted as a toxic dose.

What is claimed is:

1. A method for the treatment of human solid tumors and metastasis thereof comprising, administering a cell membrane penetrating indigoid bisindole derivative to a human in need thereof, wherein said human solid tumors and metastasis thereof are selected from carcinomas, melanomas, adenomas, sarcomas, lymphomas, neuroblastomas, teratomas, astrocytomas, glioblastomas, or mesotheliomas, and the indigoid bisindole derivative is selected from bis(3-phenylindol-2-yl), isoindigo or indirubin derivatives, the indirubin derivatives being represented by the following formula (I):

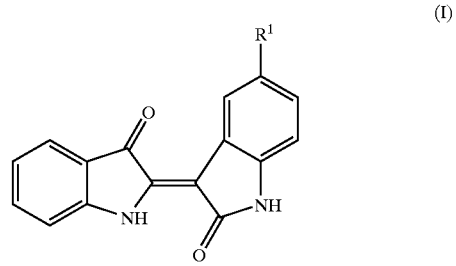

(I)

wherein, X represents an oxygen atom or NOH, and when X represents an oxygen atom, $R^1$ represents a hydrogen atom, a halogen atom, a $-NO_2$ group, a methyl group, a sulfonamide group or $SO_2-NH-CH_2CH_2-OH$; and when X represents NOH, $R^1$ represents a hydrogen atom or an iodide atom.

2. The method according to claim 1, wherein the solid tumors are selected from mammary carcinoma, melanoma, large-cell lung carcinoma, small-cell lung carcinoma, lung epidermoid and adenocarcinoma, colorectal carcinoma, bladder carcinoma, ovarian carcinoma, pancreatic carcinoma, renal carcinoma, prostatic carcinoma, head and neck carcinomas, melanomas, cervical carcinomas, or osteosarcoma.

3. The method according to claim 1, wherein the indigoid bisindole derivative is in the form of a physiologically acceptable salt.

4. The method according to claim 2, wherein the indigoid bisindole derivative is in the form of a physiologically acceptable salt.

5. The method according to claim 1, wherein the solid tumors are selected from mammary carcinoma, melanoma, large-cell lung carcinoma, small-cell lung carcinoma, lung adenocarcinoma, colon carcinoma, bladder carcinoma, ovarian carcinoma, pancreatic carcinoma, renal carcinoma, or prostatic carcinoma.

* * * * *

UNITED STATES PATENT AND TRADEMARK OFFICE
CERTIFICATE OF CORRECTION

PATENT NO.   : 6,664,285 B1
DATED        : December 16, 2003
INVENTOR(S)  : Gerhard Eisenbrand et al.

It is certified that error appears in the above-identified patent and that said Letters Patent is hereby corrected as shown below:

Column 2,
Line 1, replace formula (I) with the following:
--

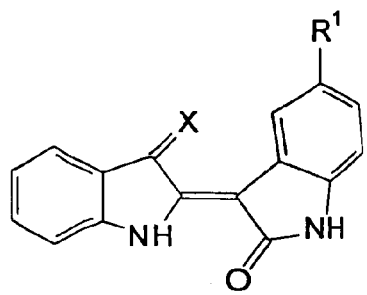

(I)

--

Column 14,
Line 7, replace formula (I) with the following:

--

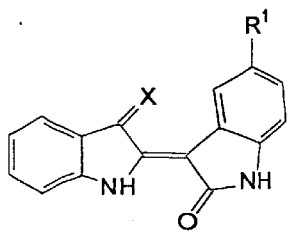

(I)

--

Signed and Sealed this

Twenty-fourth Day of August, 2004

JON W. DUDAS
*Director of the United States Patent and Trademark Office*